United States Patent [19]
Fujii et al.

[11] 4,248,794
[45] Feb. 3, 1981

[54] PROCESS FOR PRODUCING 2-AMINO-4-ACYLAMINOPHENYL ETHER

[75] Inventors: Yozo Fujii, Nishinomiya; Hiromichi Yamaguchi, Osaka, both of Japan

[73] Assignee: Sumitomo Chemical Company, Limited, Japan

[21] Appl. No.: 55,196

[22] Filed: Jul. 2, 1979

[30] Foreign Application Priority Data

Jul. 10, 1978 [JP] Japan ................................ 53/84162

[51] Int. Cl.³ .......................................... C07C 102/00
[52] U.S. Cl. .................................. 564/133; 564/144; 564/157; 564/184; 564/223
[58] Field of Search ....................... 260/562 A, 558 P

[56] References Cited

U.S. PATENT DOCUMENTS 4,070,485  1/1978  Malen et al. ..................... 260/562 A

FOREIGN PATENT DOCUMENTS 1543625  8/1972  Fed. Rep. of Germany.

OTHER PUBLICATIONS

Weiss et al., J. Am. Chem. Soc. 80 (1958), pp. 4657-4658.
Pizey, Synthetic Reagents, vol. 1, Halsted Press, New York, NY, 1974, p. 50.

Primary Examiner—Arthur P. Demers
Attorney, Agent, or Firm—Wenderoth, Lind & Ponack

[57] ABSTRACT

The present invention relates to a process for producing a 2-amino 4-acylaminophenyl ether by acylation of a 2,4-diaminophenyl ether with a good selectivity.

9 Claims, No Drawings

PROCESS FOR PRODUCING 2-AMINO-4-ACYLAMINOPHENYL ETHER

The 2-amino-4-acylaminophenyl ether is an important intermediate as a coupling component for the production of an azo disperse dye and has been produced, as known, by acylation of the 2,4-diaminophenyl ether with an acylating agent.

In this acylation, however, at least any one of a 2-acylamino compound and a 2,4-bis (acylamino) compound is inevitably by-produced in addition to the desired 4-acylamino compound, making it difficult to produce the desired 4-acylamino compound selectively with good yield.

For example, there are known an acylation process for the production of the 2-amino-4-acylaminophenyl ether comprising carrying out the acylation in a reaction solvent of water, a lower alcohol, an ester or a ketone, or a mixture of water and said organic solvent (German Offenlegungsschrift No. 1,543,625), and a process comprising contacting a mineral acid salt of said diamine with an acylating agent in an aqueous medium (Japanese Patent Application Kokai Nos. 88035/1975 and 73831/1977). According to the former process, the undersirable by-production of 2-acylamino compound is a little, whereas the undesirable 2,4-bis (acylamino) compound is produced in a large amount to produce the desired 2-amino-4-acylaminophenyl ether in such a low yield of at most 75%, and according to the latter one, the by-production of of 2,4-bis (acylamino) compound is a little, whereas the 2-acylamino compound is produced in a large amount, so that the yield of the desired 4-acylamino compound becomes much less than 80%, and moreover the separation of the desired compound and the by-products becomes difficult.

In order to improve said conventional processes, the present inventors have studied said acylation of the 2,4-diaminophenyl ether to obtain the 2-amino-4-acylaminophenyl ether, and found that the acylation is effectively carried out by using as an acylation solvent an N-substituted amide of a lower aliphatic acid or a mixed solvent containing said N-substituted acid amide as a main component, favorably at a relatively low temperature, whereby the desired 2-amino-4-acylaminophenyl ether is obtained with an extremely high selectivity of 95% or more, while the by-production of the 2-acylamino compound is little and that of the 2,4-bis (acylamino) compound is as little as 5% or less.

The present invention provides a process for producing a 2-amino-4-acylaminophenyl ether of the formula,

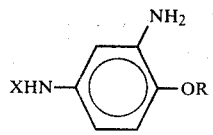

wherein R is a $C_1$-$C_9$ alkyl group, a halogen-, $C_1$-$C_3$ alkoxy-, phenyl- or phenoxy-substituted $C_1$-$C_4$ alkyl group or a phenyl group unsubstituted or substituted with one or two substituents selected from halogen atoms, $C_1$-$C_4$ alkyl groups, $C_1$-$C_4$ alkoxy groups and acylamino groups, and X is an acyl group, which comprises contacting a 2,4-diaminophenyl ether of the formula,

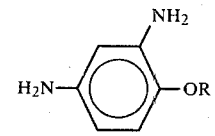

wherein R is as defined above, with an acylating agent in the presence of a reaction solvent which is an N-substituted amide of a lower aliphatic acid or a mixture containing said N-substituted acid amide.

In the present specification, the term "acyl" includes acetyl, propionyl, benzoyl and the like, the term "halogen" includes chlorine and bromine, and examples of the substituted phenyl group include p-chlorophenyl, p-tolyphenyl, p-acetylaminophenyl, 2,4-dimethylphenyl and 2,4-dichlorophenyl.

In carrying out the process of the present invention, it is essential to use as an acylation solvent an N-substituted amide of a lower aliphatic acid, and the N-substituted amide includes, for example, N,N-dimethylformamide, N,methylformamide, N,N-dimethylacetamide, N-methylpropionamide and the like. Of these, N,N-dimethylformamide is favorably used because it is economical and operations including isolation of the desired compound and separation of the solvent after the acylation are facilitated. Further, as the acylation solvent, there can also be used a mixture comprising said N-substituted acid amide and at least one solvent selected from water, lower alcohols (e.g. methyl alcohol, ethyl alcohol and isopropyl alcohol), lower carboxylic acids (e.g. formic acid, acetic acid and propionic acid), ketones (e.g. acetone, methyl ethyl ketone and methyl isobutyl ketone) and hydrocarbons (e.g. n-hexane, cyclohexane, benzene and toluene). The amount of one solvent to be mixed with said N-substituted acid amide is at most 40% by weight of the mixture.

The amount of the acylation solvent is not particularly limited, but it is usually 2 to 15 times, favorably 3 to 10 times, the weight of the starting 2,4-diaminophenyl ether. The acylation solvent may be used in an amount more than that as defined above without any adverse effect to the acylation, but it is uneconomical.

The acylating agent used in the process of the present invention includes, for example, an aliphatic acid anhydride (e.g. acetic anhydride, propionic anhydride), an aromatic acid anhydride (e.g. benzoic anhydride), and a halide (e.g. acetyl chloride or bromide, benzoyl chloride or bromide).

The amount of the acylating agent is usually 0.6 to 1.05 mole, favorably 0.8 to 1.03 mole, per mole of the 2,4-diaminophenyl ether.

In carrying out the acylation of the present invention, the stating 2,4-diaminophenyl ether is dissolved in the acylation solvent of the N-substituted acid amide or the mixture containing the same, under an atmosphere of an inert gas (e.g. nitrogen gas) and then the acylating agent is added thereto while the reaction system being stirred.

The acylation is carried out preferably at a relatively low temperature, usually at −10° to 40° C., favorably at 0° C. to 25° C., more favorably at 0° to 20° C.

After completion of the acylation, the desired 2-amino-4-acylaminophenyl ether product is isolated from the reaction mixture. For example, the acylation solvent and low boiling matters are distilled off under reduced pressure to obtain the crude product, which can be, if desired, purified by further distillation under reduced pressure, or the like. Alternatively, a part of the acylation solvent and low boiling matters is eliminated by distillation to obtain a concentrate, and then water is added to the concentrate to precipitate the desired 2-amino-4-acylaminophenyl ether, which is separated by filtration and then dried. The thus obtained 2-amino-4-acylaminophenyl ether is suitable for use as a starting material for the production of azo disperse dyes.

The present invention is illustrated in more detail with reference to the following Examples, but is not intended to be limited to the following Examples, in which all parts and percents are by weight unless otherwise indicated.

EXAMPLE 1

2,4-Diaminoanisole (100 parts) was dissolved in N,N-dimethylformamide (600 parts) under a nitrogen atmosphere and then cooled to 10° C. Acetic anhydride (74 parts: 1.00 in the molar ratio to 2,4-diaminoanisole) was added dropwise to the resulting solution over a period of 2 hours. The mixture was stirred for 30 minutes and thereafter the solvent and by-produced acetic acid were distilled off to obtain a concentrate (129 parts).

The composition of the concentrate was as shown below:

| | |
|---|---|
| 2-amino-4-acetylaminoanisole | 96.0% |
| 2-acetylamino-4-aminoanisole | less than 0.1% |
| 2,4-bis(acetylamino)anisole | 1.5% |
| 2,4-diaminoanisole | 1.5% |
| others | less than 1.0% |

The concentrate was subjected to simple distillation to collect a fraction (119 parts) at 180° to 195° C./1 mmHg. The resulting product had a 2-amino-4-acetylaminoanisole content of 99%, and the over-all yield from the starting 2,4-diaminoanisole was 90.3%.

COMPARATIVE EXAMPLE 1

Acetylation and concentration were carried out in each manner similar to those of Example 1, provided that methanol was used in place of N,N-dimethylformamide as the solvent, whereby there was obtained a concentrate (130 parts) having the following composition:

| | |
|---|---|
| 2-amino-4-acetylaminoanisole | 79.0% |
| 2,4-diaminoanisole | 7.4% |
| 2,4-bis(acetylamino)anisole | 12.1% |
| others | 1.5% |

COMPARATIVE EXAMPLE 2

Acetylation and concentration were carried out in each manner similar to those of Example 1, provided that acetone was used in place of N,N-dimethylformamide, whereby there was obtained a concentrate (135 parts) having the following composition:

| | |
|---|---|
| 2-amino-4-acetylaminoanisole | 75.0% |
| 2,4-diaminoanisole | 5.7% |
| 2,4-bis(acetylamino)anisole | 18.0% |
| others | 1.3% |

COMPARATIVE EXAMPLE 3

Acetylation and concentration were carried out in each manner similar to those of Example 1, provided that a water-ethanol mixed solvent (the mixing ratio by weight being 4:1) was used in place of N,N-dimethylformamide, whereby there was obtained a concentrate (131 parts) having the following composition:

| | |
|---|---|
| 2-amino-4-acetylaminoanisole | 78.2% |
| 2,4-diaminoanisole | 4.9% |
| 2,4-bis(acetylamino)anisole | 15.3% |
| others | 1.6% |

EXAMPLE 2

2,4-Diaminodiphenyl ether (100 parts) was dissolved in a mixed solvent (600 parts) consisting of N,N-dimethylacetamide (550 parts) and methanol (50 parts) under a nitrogen atmosphere, and then cooled to 5° C. Acetic anhydride (51 parts: 1.00 in the molar ratio to 2,4-diaminodiphenyl ether) was added dropwise to the resulting solution over a period of 2 hours, and thereafter the mixture was stirred for 30 minutes. The solvent and by-produced acetic acid (400 parts in a total amount) were distilled off to obtain a concentrate. Successively, the concentrate was mixed with water (500 parts), and a 10% aqueous sodium hydroxide solution was added thereto to adjust pH of the mixture to 7. The mixture was stirred for 1 hour to precipitate crystals, which were separated by filtration, washed with water and then dried. Thus, a dried product (119 parts) was obtained, and the composition thereof was as shown below:

| | |
|---|---|
| 2-amino-4-acetylaminodiphenyl ether | 96.9% |
| 2,4-diaminodiphenyl ether | 0.7% |
| 2,4-bis(acetylamino)diphenyl ether | 2.1% |
| others (unknown matters) | 0.3% |

COMPARATIVE EXAMPLE 4

2,4-Diaminodiphenyl ether (100 parts) was dissolved in a mixture consisting of 35% hydrochloric acid (104 parts) and water (196 parts), and then cooled to 10° C. Acetic anhydride (53 parts: 1.04 in the molar ratio to 2,4-diaminodiphenyl ether) was added dropwise to the resulting solution over a period of 4 hours, during which the temperature was kept at 10° C. or below and 40% aqueous sodium hydroxide solution was added thereto to keep pH of the system from 1.5 to 3.5. Thereafter, the reaction mixture was stirred for 1 hour and 35% hydrochloric acid was added to the reaction mixture to adjust the pH 1. Sodium chloride (100 parts) was added thereto and the mixture was stirred for additional 1 hour to precipitate crystals, which were then separated by filtration, washed with a 20% aqueous sodium chloride solution and dried. A dried product (132 parts) was obtained and the composition thereof was as shown below:

| | |
|---|---|
| 2-amino-4-acetylaminodiphenyl ether hydrochloride | 71.1% |
| 4-amino-2-acetylaminodiphenyl ether hydrochloride | 9.3% |
| 2,4-diaminodiphenyl ether dihydrochloride | 4.7% |
| 2,4-bis(acetylamino)diphenyl ether | 11.9% |
| others | 3.0% |

The yield of the desired product was 67.4%.

EXAMPLE 3

2,4-Diaminophenetole (100 parts) was dissolved in a mixed solvent (600 parts) consisting of N,N-dimethylformamide (550 parts) and water (50 parts) and then cooled to 10° C. Benzoic anhydride (152 parts: 1.02 in the molar ratio to 2,4-diaminophenetole) was added thereto over a period of 2 hours. The mixture was thereafter stirred for 30 minutes and then subjected to distillation under reduced pressure to remove the solvent (450 parts). The resulting concentrate was mixed with water (600 parts) under a nitrogen atmosphere, and a 10% aqueous sodium hydroxide solution was added thereto to adjust pH of the mixture to 7. The mixture was further stirred for 1 hour to precipitate crystals, which were then separated by filtration, washed with water and then dried. Thus, a dried product (165 parts) was obtained and the composition thereof was as shown below:

| | |
|---|---|
| 2-amino-4-benzoylaminophenetole | 95.8% |
| 2,4-diaminophenetole | 1.3% |
| 2,4-bis(benzoylamino)phenetole | 2.3% |
| others (unknown matters) | 0.6% |
| The yield of the desired product was 95.1%. | |

EXAMPLE 4

2,4-Diamino-2',4'-dichlorodiphenyl ether (100 parts) was dissolved in N,N-dimethylformamide (600 parts) under a nitrogen atmosphere and then cooled to 10° C. Propionic anhydride (49 parts: 1.01 in the molar ratio to 2,4-diamino-2',4'-dichlorodiphenyl ether) was added to the resulting solution over a period of 2 hours. The mixture was stirred for 30 minutes, and then subjected to distillation under reduced pressure to remove the solvent and by-produced propionic acid (400 parts in a total amount). Successively, the resulting concentrate was mixed with water (500 parts) and a 10% aqueous sodium hydroxide solution was added thereto to adjust the pH to 7. The mixture was further stirred for 1 hour to precipitate crystals, which were then separated by filtration, washed with water and dried. Thus, a dried product (118 parts) was obtained and the composition thereof was as shown below:

| | |
|---|---|
| 2-amino-4-propionylamino-2',4'-dichlorodiphenyl ether | 96.2% |
| 2,4-diamino-2',4'-dichlorodiphenyl ether | 1.3% |
| 2,4-bis(propionylamino)-2',4'-dichlorodiphenyl ether | 2.1% |
| others (unknown matters) | 0.4% |
| The yield of the desired product was 95.4%. | |

What is claimed is:

1. A process for producing a 2-amino-4-acylaminophenyl ether of the formula,

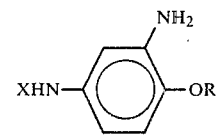

wherein R is a $C_1$–$C_9$ alkyl group, a halogen-, $C_1$–$C_3$ alkoxy-, phenyl- or phenoxy-substituted $C_1$–$C_4$ alkyl group or a phenyl group unsubstituted or substituted with one or two substituents selected from halogen atoms, $C_1$–$C_4$ alkyl groups, $C_1$–$C_4$ alkoxy groups and acylamino groups, and X is an acyl group, which comprises contacting a 2,4-diaminophenyl ether of the formula,

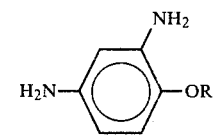

wherein R is a defined above, with an acylating agent in the presence of a reaction solvent which is an N-substituted amide of a lower aliphatic acid or a mixture containing said N-substituted acid amide.

2. A process according to claim 1, wherein the acylating agent is an aliphatic acid anhydride, an aromatic acid anhydride or a halide.

3. A process according to claim 1, wherein the N-substituted acid amide is N,N-dimethylformamide, N-methylformamide, N,N-dimethylacetamide or N-methylpropionamide.

4. A process according to claim 1, wherein the mixture contains the N-substituted acid amide and at least one solvent selected from water, lower alcohols, lower carboxylic acids, ketones and hydrocarbons.

5. A process according to claim 4, wherein the amount of the solvent is at most 40% by weight of the mixture.

6. A process according to claim 1, wherein the amount of the reaction solvent is 2 to 15 times the weight of the 2,4-diaminophenyl ether.

7. A process according to claim 1, wherein the acylating agent is used in an amount of 0.6 to 1.05 mole per mole of the 2,4-diaminophenyl ether.

8. A process according to claim 1, wherein the contacting is carried out at a temperature of −10° to 40° C.

9. A process according to claim 1, wherein the contacting is carried out by dissolving the 2,4-diaminophenyl ether in the reaction solvent under an atmosphere of an inert gas and then adding the acylating agent thereto under stirring of the reaction system.

* * * * *